(12) United States Patent
Maeda

(10) Patent No.: US 7,195,229 B2
(45) Date of Patent: Mar. 27, 2007

(54) AUTOMATIC SAMPLER

(75) Inventor: Yoshiaki Maeda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 536 days.

(21) Appl. No.: 10/351,908

(22) Filed: Jan. 27, 2003

(65) Prior Publication Data

US 2003/0143123 A1    Jul. 31, 2003

(30) Foreign Application Priority Data

Jan. 29, 2002 (JP) .............................. 2002-019914

(51) Int. Cl.
*F16K 1/36* (2006.01)
*F16K 5/10* (2006.01)
*F16K 39/00* (2006.01)
*F16K 5/00* (2006.01)
*F16K 31/00* (2006.01)

(52) U.S. Cl. .................... 251/205; 422/50; 422/68.1; 422/81; 422/82; 422/103; 436/43; 137/87.01; 137/15.22; 137/247; 137/250; 251/208; 251/281; 251/286; 251/292; 251/304; 251/345; 251/352

(58) Field of Classification Search ................. 422/50, 422/68.1, 81, 82, 103; 436/43; 137/87.01, 137/15.22, 247, 250; 251/205, 208, 281, 251/286, 292, 304, 345, 352
See application file for complete search history.

(56) References Cited

U.S. PATENT DOCUMENTS

| 5,948,360 | A | * | 9/1999 | Rao et al. ...................... 422/65 |
| 5,993,744 | A | * | 11/1999 | Rao et al. .................... 422/103 |
| 6,012,487 | A | * | 1/2000 | Hauck .................... 137/625.11 |
| 6,056,921 | A | * | 5/2000 | Rao et al. ...................... 422/65 |
| 6,475,388 | B1 | * | 11/2002 | Gjerde et al. ................ 210/635 |
| 6,715,624 | B2 | * | 4/2004 | Brockwell ................... 215/247 |

FOREIGN PATENT DOCUMENTS

| JP | 54-114545 | 8/1954 |
| JP | 50-85394 | 7/1975 |
| JP | 3-183947 | 8/1991 |
| JP | 6-148157 | 5/1994 |
| JP | 8-15278 | 1/1996 |

* cited by examiner

*Primary Examiner*—Brian Sines
(74) *Attorney, Agent, or Firm*—Rankin, Hill, Porter & Clark LLP

(57) ABSTRACT

In a direct injection type automatic sampler, a sampling needle having a liquid sample collected from a sample vessel by using suction force of a pump is inserted into an injection port. Then, a flow path-switching valve is rotated to switch a flow path to make a flow of mobile phase liquid pass through a loop to thereby introduce the collected sample into a column. The injection port is directly incorporated in the flow path-switching valve.

8 Claims, 3 Drawing Sheets

AUTOMATIC SAMPLER

BACKGROUND OF THE INVENTION

1. Field of the Invention

The present invention relates to an automatic sampler, for example, an automatic sampler for introducing each sample into a liquid chromatograph automatically.

2. Description of the Related Art

FIG. 3 shows flow paths as important parts of a related-art automatic sampler for liquid chromatograph.

In FIG. 3, an automatic sampler has a 6-port 2-position flow path-switching rotary valve 1 which has six ports arranged at regular intervals, and two path positions for connecting every adjacent two of the six ports to each other. When the flow path-switching valve 1 is rotated, one of the two path positions is moved to the other to switch flow paths.

Sample vessels 3 each containing a liquid sample to be analyzed are arranged on a rack 31. A sampling needle 5 sucks in and collects the liquid sample from selected one of the sample vessels 3. The sampling needle 5 is connected to a pump 2 through both a looped flexible conduit pipe (hereinafter referred to as "loop") 6 and the flow path-switching valve 1, so that the pump 2 gives suction force to the sampling needle 5. After the sampling needle 5 driven by a not-shown automatic drive mechanism sucks in the liquid sample in the position (sampling position) represented by the broken line in FIG. 3, the sampling needle 5 moves to the position (injection position) represented by the solid line in FIG. 3. In the injection position, the sampling needle 5 is inserted into an injection port 4. After the insertion, the sampling needle 5 is kept liquid-tight in the injection port 4.

A mobile phase liquid for the liquid chromatograph passes through the flow path-switching valve 1 from a liquid feed pump 91 via a mobile phase liquid feed flow path 7 and further flows into a column 92 via a column upstream side flow path 8.

The automatic sampler further has a rinse mechanism 10 which includes another valve (low-pressure valve) 11, and a rinse port 12. The rinse mechanism 10 plays the important role of rinsing the sample liquid from the sampling needle 5, etc. prior to analysis of a next sample to prevent contamination caused by the previous sample. The detailed description of the rinse mechanism 10 will be omitted because it is not directly related to the description of the present invention.

Introduction of each sample by the automatic sampler is performed in the following sequence.

(1) In the condition that the path of the flow path-switching valve 1 represented by the solid line in FIG. 3 is validated while the sampling needle 5 is located in the sampling position, the sampling needle 5 is dipped into the sample vessel 3 and the pump 2 is actuated so that a predetermined amount of the liquid sample is sucked in and collected. The collected liquid sample is mainly retained in the loop 6.

(2) The sampling needle 5 is moved to the injection position and inserted into the injection port 4.

(3) When the flow path-switching valve 1 is rotated by 60 degrees so that the path represented by the broken line in FIG. 3 is validated, the mobile phase liquid fed by the liquid feed pump 91 flows into the column 92 via the mobile phase liquid feed flow path 7, the loop 6, the sampling needle 5, the injection port 4 having the sampling needle 5 inserted therein, a pipe 41 and the column upstream side flow path 8 successively. As a result, the liquid sample mainly retained in the loop 6 is carried to the column 92 and analyzed.

(4) The flow path-switching valve 1 is rotated back and rinsing (which will be not described in detail) is performed by the rinse mechanism 10 to prepare for collection of the next sample. Then, the automatic sampler stands by for collection of the next sample.

The automatic sampler shown in FIG. 3 is called "direct injection type automatic sampler" because the sample sucked in and collected by the sampling needle 5 can be directly introduced into the column 92. In the related-art direct injection type automatic sampler, the injection port 4 and the flow path-switching valve 1 are disposed separately and connected to each other by the pipe 41. As described above, because the liquid sample must pass through the pipe 41, the inner volume of the pipe 41 forms dead volume. Hence, there is a drawback that the sample peak is spread. In addition, if there are piping joints in the path through which the sample passes, there is generally possibility that the sample may remain in fine gaps at the piping joints so that cross contamination occurs easily. Therefore, the number of piping joints needs to be reduced as extremely as possible.

SUMMARY OF THE INVENTION

The present invention is developed in consideration of the problems associated with the related art. An object of the present invention is to provide an automatic sampler in which both the inner volume of a path through which a sample passes and the number of piping joints are reduced as extremely as possible.

To solve the problems, an automatic sampler according to the present invention comprises an injection port and a flow path-switching valve wherein the injection port and the flow path-switching valve to be connected thereto are connected to each other directly without interposition of any pipe. That is, the automatic sampler according to the present invention is a direct injection type automatic sampler having an injection port and a flow path-switching valve integrated with the injection port.

Hence, the number of piping joints in the path through which the sample passes is reduced while dead volume is reduced, so that cross contamination is reduced.

DETAILED DESCRIPTION OF THE INVENTION

Figure 1:
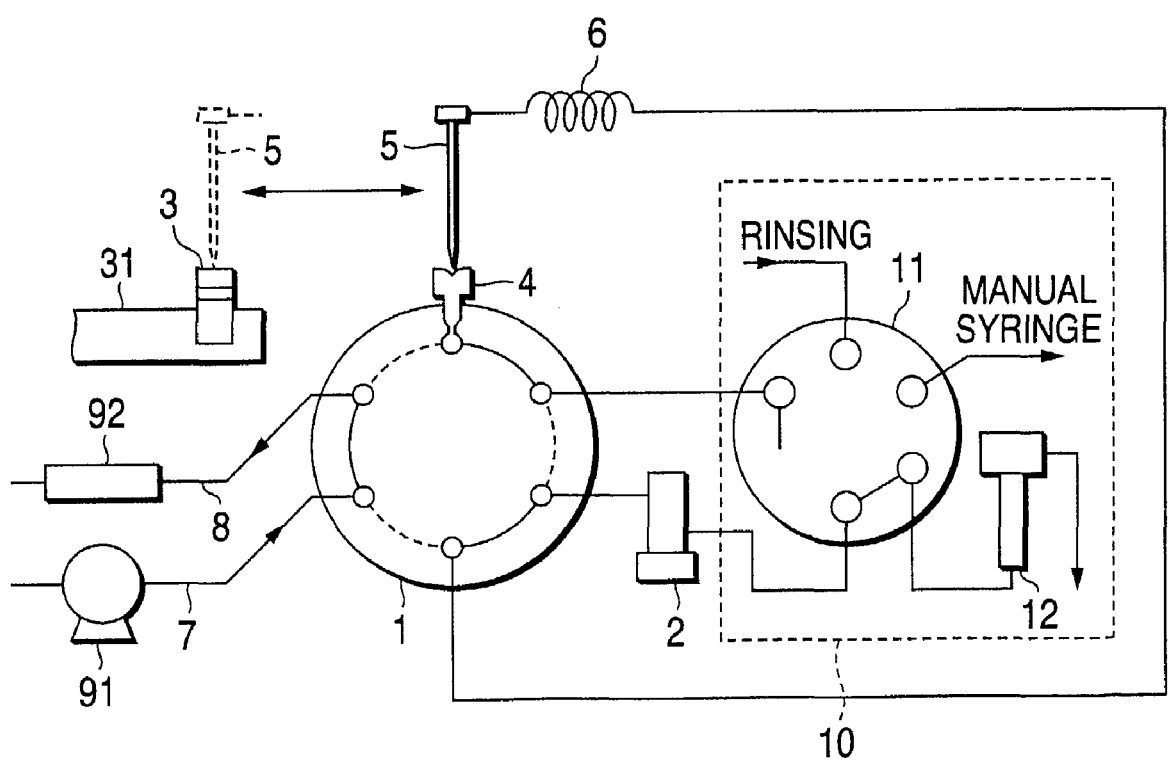
FIG. 1 is a view showing an embodiment of the present invention.
Figure 3:
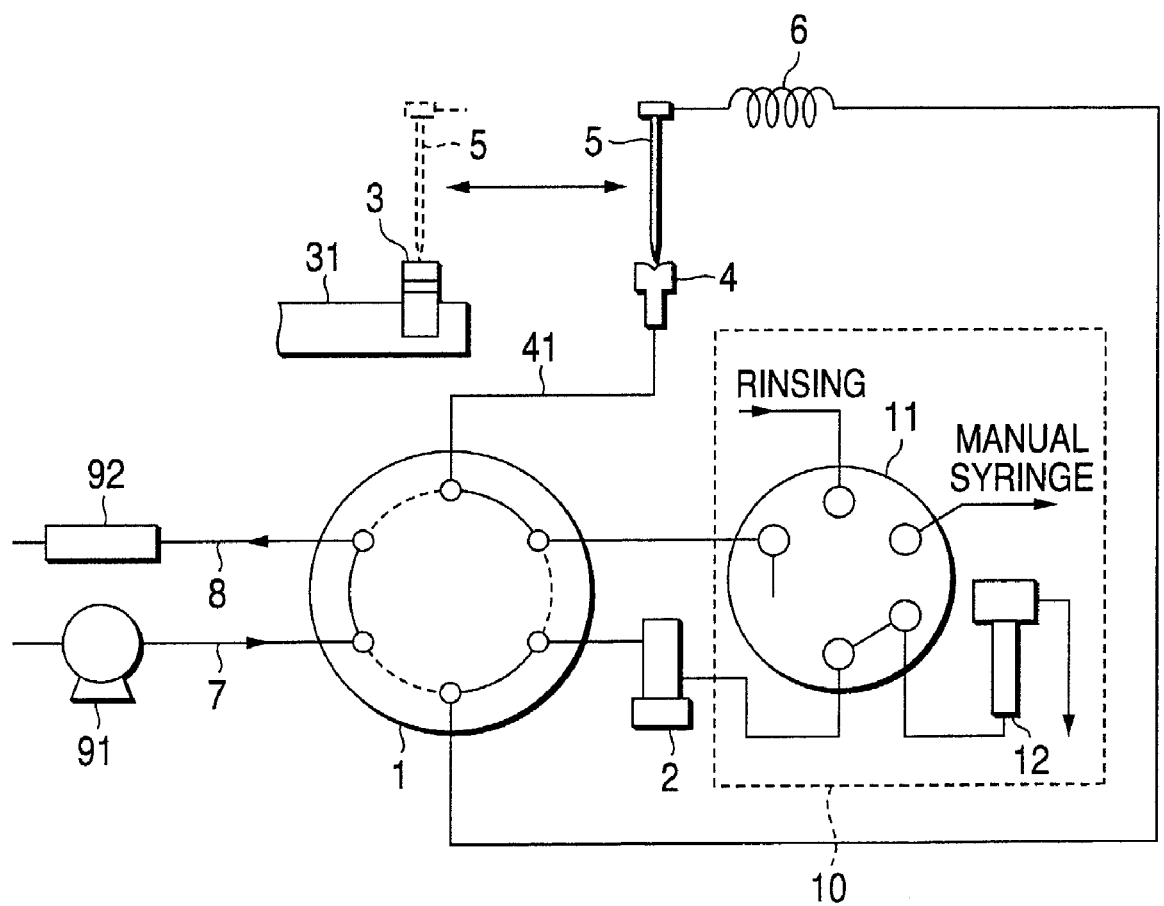
FIG. 3 is a view showing an example of a related-art automatic sampler.

An embodiment of the present invention is shown in FIG. 1. FIG. 1 shows flow paths as important parts of a direct injection type automatic sampler according to the present invention. The embodiment shown in FIG. 1 is substantially the same as the related-art example shown in FIG. 3 except that the injection port 4 is directly connected to the flow path-switching valve 1. The operating sequence in this embodiment is the same as that in the related-art example. Constituent parts the same in function as those in FIG. 3 are referred to by numerals the same as those in FIG. 3 for the sake of omission of duplicated description.

Figure 2:
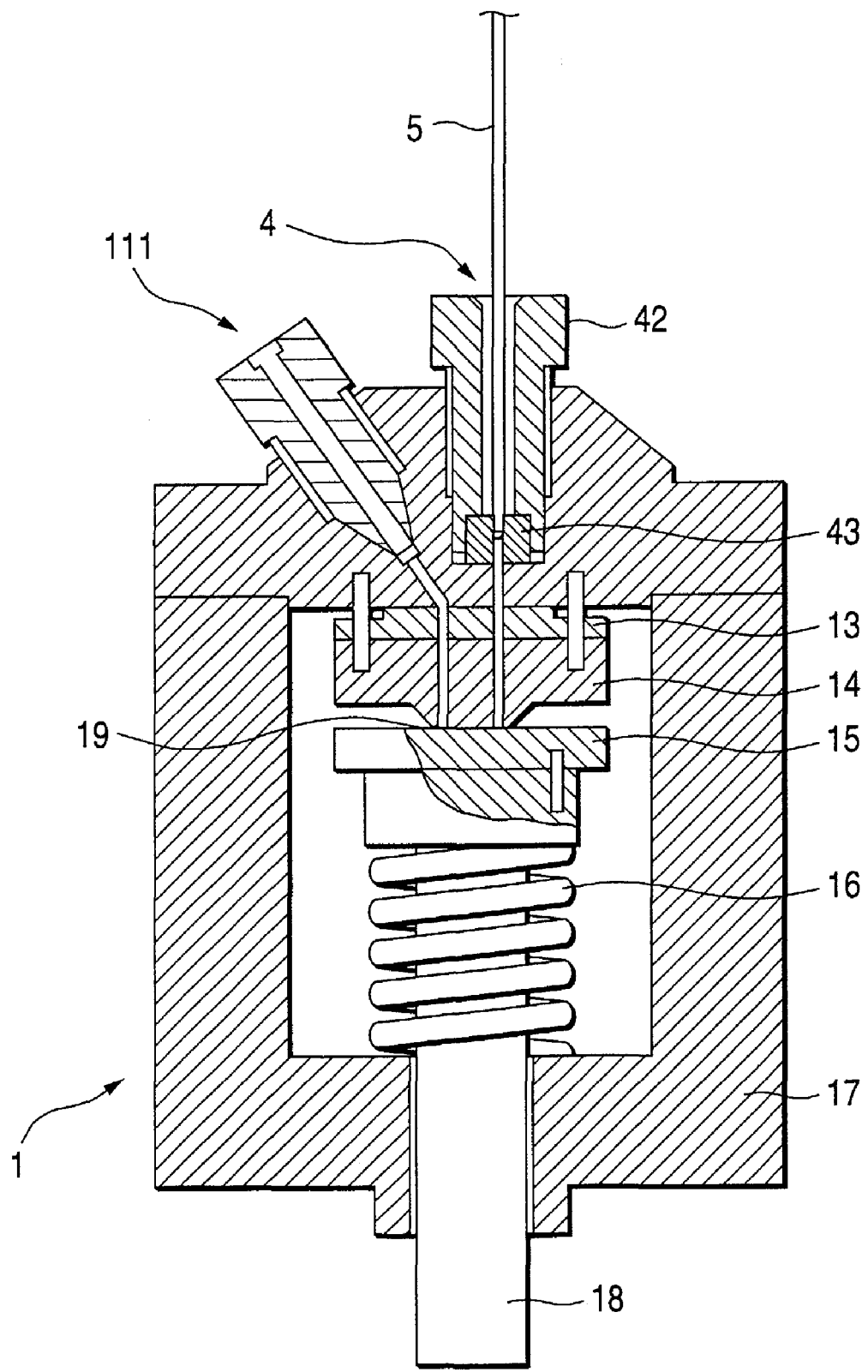
FIG. 2 is a view showing the specific structure of the embodiment of the present invention.

FIG. 2 is a view showing an example of specific structure of the flow path-switching valve 1 to which the injection port 4 in FIG. 1 is connected directly. The flow path-switching valve 1, the injection port 4 and the sampling needle 5 inserted into the injection port 4 are shown in FIG. 2.

The flow path-switching valve 1 has a packing 13, a stator 14, a rotor 15, a spring 16, a body 17 and a shaft 18. The stator 14 is attached to an inner side of the body 17 of the flow path-switching valve 1 through the packing 13. The rotor 15 is fixed to the shaft 18. The rotor 15 frictionally rotates relative to the stator 14 while the stator 14 and the rotor 15 are pressed against each other by the spring 16.

The injection port 4 is provided vertically in a top portion of an upper surface (rear surface viewed from the shaft 18 side) of the flow path-switching valve 1. Another port 111 is disposed around the injection port 4. Flow paths piercing the packing 13 and the stator 14 and led to a frictional surface 19 of the rotor 15 are provided so as to extend from the ports 4 and 111 respectively.

Paths for connecting adjacent ports of the flow path-switching valve 1 as shown in FIG. 3 or 1 are formed as three circular arc-like grooves in the frictional surface 19 of the rotor 15. Hence, because paths connected to the ports respectively are made to communicate with one another by the three grooves, the flow paths can be switched by rotation of the shaft 18.

The stator 14 is made of a rigid material such as ceramics. The rotor 15 is made of an elastic material such as a polyimide resin. In addition, frictional surfaces of the stator 14 and the rotor 15 are smoothened. Hence, the stator 14 and the rotor 15 adhere closely to each other, so that they are kept liquid-tight.

The injection port 4 has a needle seal 43 provided with a through-hole in its center, and a nut 42 for pressing the needle seal 43. The nut 42 and the needle seal 43 may be formed integrally with the same resin material. When the sampling needle 5 is inserted into the injection port 4, a tapered portion at a tip of the sampling needle 5 is fitted into the center hole of the needle seal 43. Hence, the sampling needle 5 can be connected to the injection port 4 without liquid leakage. Because the center hole of the needle seal 43 is directly connected to the frictional surface by the path piercing both the packing 13 and the stator 14, dead volume is very small and the liquid sample can reach the column at the shortest distance from the sampling needle 5 by the flow path-switching function.

Incidentally, the loop 6 in the above description need not be always formed like a loop if it can be provided as a conduit pipe having an inner volume of not smaller than the amount of the collected sample. Although FIG. 1 which is a view of flow paths and FIG. 2 which is a view of the structure of the flow path-switching valve show an embodiment of the present invention, the present invention is not limited thereto.

Further, the automatic sampler according to the present invention is not limited to the automatic sampler for liquid chromatograph as above stated. It may be an automatic sampler for gas chromatograph, etc.

As described above in detail, the automatic sampler according to the present invention comprises the injection port and the flow path-switching valve wherein the injection port and the flow path-switching valve are connected to each other directly without interposition of any pipe. Hence, the following effects are brought about. That is, the dead volume of the flow path between the injection port and the flow path-switching valve is reduced, so that the volume of delay caused by the gradient of the flow path is reduced; the analyzing time is reduced; and the sample peak is prevented from being spread. In addition, because the pipe is omitted, the number of piping joints can be reduced. Hence, cross contamination caused by the sample remaining in fine gaps at piping joints can be reduced.

What is claimed is:

1. An automatic sampler comprising:
    a sampling needle for drawing in and collecting a liquid sample;
    an injection port having a needle seal with a through-hole in its center and into which said liquid sample is injected by said sampling needle;
    a flow path-switching valve for performing switching of a flow path;
    a first pump for communicating a suction force to said sampling needle when said flow path-switching valve is in a first position so as to draw in and collect the liquid sample with the sampling needle;
    a second pump for pressurizing the collected liquid sample so as to inject the liquid sample from said needle into said sample port when said flow path-switching valve is in a second position, wherein, when said flow path-switching valve is in said second position said second pump is connected to both said sampling needle and said injection port by a flow path through said flow path-switching valve,
    wherein said injection port is incorporated in said flow path-switching valve, and a front end of the sampling needle and the needle seal are fitted to one another.

2. The automatic sampler according to claim 1, wherein said injection port also has a nut for pressing the needle seat.

3. The automatic sampler according to claim 1, wherein said automatic sampler is used for a liquid chromatograph for analyzing said injected liquid sample, the liquid chromatograph being connected to a liquid feed pump by a mobile phase liquid feed flow path through said flow path-switching valve and to an inlet side of a column by a column upstream side flow path through said flow path-switching valve.

4. The automatic sampler according to claim 1, wherein the flow path-switching valve comprises a valve body, a stator, a rotor, and a shaft, the stator and rotor being received in the valve body, said stator being fixed to an inner surface of the valve body, and wherein the rotor is fixed to the shaft and received in the valve body and frictionally rotates relative to the stator.

5. The automatic sampler according to claim 4, wherein the valve further comprises a spring that urges the rotor against the stator.

6. The automatic sampler according to claim 5, wherein the flow paths are provided by grooves formed in a face of the rotor, and wherein communication with each of the respective flow paths is selected by rotation of the shaft.

7. The automatic sampler according to claim 6, wherein said injection port also has a nut for pressing the needle seal.

8. The automatic sampler according to claim 7, wherein said automatic sampler is used for a liquid chromatograph for analyzing said injected liquid sample, the liquid chromatograph being connected to a liquid feed pump by a mobile phase liquid feed flow path through said flow path-switching valve and to an inlet side of a column by a column upstream side flow path through said flow path-switching valve.

* * * * *